US011814639B2

(12) United States Patent
Atarashi et al.

(10) Patent No.: US 11,814,639 B2
(45) Date of Patent: Nov. 14, 2023

(54) VIRUS-RESISTANT PLANT AND METHOD FOR PRODUCING THE SAME

(71) Applicants: Kikkoman Corporation, Chiba (JP); National University Corporation Hokkaido University, Hokkaido (JP)

(72) Inventors: Hiroki Atarashi, Chiba (JP); Kenji Nakahara, Hokkaido (JP); Tetsuya Yamada, Hokkaido (JP); Chikara Masuta, Hokkaido (JP)

(73) Assignees: Kikkoman Corporation, Chiba (JP); National University Corporation Hokkaido University, Hokkaido (JP)

( * ) Notice: Subject to any disclaimer, the term of this patent is extended or adjusted under 35 U.S.C. 154(b) by 116 days.

(21) Appl. No.: 16/963,191

(22) PCT Filed: Jan. 31, 2019

(86) PCT No.: PCT/JP2019/003436
§ 371 (c)(1),
(2) Date: Jul. 17, 2020

(87) PCT Pub. No.: WO2019/151417
PCT Pub. Date: Aug. 8, 2019

(65) Prior Publication Data

US 2021/0123071 A1 Apr. 29, 2021

(30) Foreign Application Priority Data

Feb. 2, 2018 (JP) ................................ 2018-017542
Dec. 18, 2018 (JP) ................................ 2018-236352

(51) Int. Cl.
*A01H 1/06* (2006.01)
*C12N 15/82* (2006.01)

(52) U.S. Cl.
CPC ................................ *C12N 15/8283* (2013.01)

(58) Field of Classification Search
None
See application file for complete search history.

(56) References Cited

U.S. PATENT DOCUMENTS

2005/0255455 A1 11/2005 Caranta

FOREIGN PATENT DOCUMENTS

| | | | |
|---|---|---|---|
| EP | 0504869 | A2 | 9/1992 |
| JP | H04330234 | A | 11/1992 |
| WO | 2010048398 | | 4/2010 |
| WO | 2017188321 | A1 | 11/2017 |

OTHER PUBLICATIONS

Ruffel et al, 2005, Mol. Genet. Genomics, 274:346-353.*
Piron et al., "An induced mutation in tomato eIF4E leads to immunity to two potyviruses", Jun. 25, 2010, pp. e11313, vol. 5, No. 6, Publisher: PLoS One.
Yoshii et al., "The *Arabidopsis* cucumovirus multiplication 1 and 2 loci encode translation initiation factors 4E and 4G", 2004, pp. 6102-6111, vol. 78, No. 12, Publisher: J Virol.
International Search Report received in PCT/JP2019/003436, dated Apr. 23, 2019.
Written Opinion received in PCT/JP2019/003436, dated Apr. 23, 2019.
Chandrasekaran et al., "Development of broad virus resistance in non-transgenic cucumber using CRISPR/Cas9 technology : Virus resistance in cucumber using CRISPR/Cas9", Sep. 1, 2016, pp. 1140-1145, vol. 17, No. 7, Publisher: Olecular Plant Pathology.
Mazier et al., "Knock-down of both eIF4E1 and eIF4E2 genes confers broad-spectrum resistance against potyviruses in tomato", Dec. 29, 2011, pp. 0029595, vol. 6, No. 12, Publisher: PLoS One.
Rodriguez Hernandez et al., "Melon RNA interference (RNAi) lines silenced for Cm-eIF4E show broad virus resistance", Sep. 1, 2012, pp. 755-763, vol. 13, No. 7, Publisher: Molecular Plant Pathology.
Sato et al., "Selective involvement of members of the eukaryotic initiation factor 4E family in the infection of *Arabidopsis thaliana* by potyviruses", Feb. 14, 2005, pp. 1167-1171, vol. 579, No. 5, Publisher: FEBS Lett.
Accession No. CP023759.1: Solanum lycopersicum cultivar 1-3 chromosome 3, Nov. 3, 2017, Publisher: GenBank.
Accession No. KX855953.1: Solanum lycopersicum haplotype 1 eukaryotic translation initiation factor 4E mRNA, complete cds, Oct. 5, 2016, Publisher: GenBank.

* cited by examiner

*Primary Examiner* — Jason Deveau Rosen
(74) *Attorney, Agent, or Firm* — Suzannah K. Sundby, Esq.; Canady + Lortz LLP

(57) ABSTRACT

An object of the present invention is to provide a cucumber mosaic virus (CMV)-resistant solanaceous plant. The present invention provides a CMV-resistant solanaceous plant having a mutated eIF4E gene encoding an eIF4E protein nonfunctional for CMV. In addition, the present invention provides a method for producing a CMV-resistant plant, the method comprising mutating an eIF4E gene of a solanaceous plant into a mutated eIF4E gene encoding an eIF4E protein nonfunctional for CMV.

8 Claims, 10 Drawing Sheets

Specification includes a Sequence Listing.

Figure 1

AGTGCTCCACAGTCCACAGAGCAGCAAAAATGGCAGCAGCTGAAATGGAGAGAAC
GATGTCGTTTGATGCAGCTGAGAAGTTGAAGGCCGCCGATGGAGGAGGAGGAGAG
GTAGACGATGAACTTGAAGAAGGTGAAATTGTTGAAGAATCAAATGATACGGCATC
GTATTTAGGGAAAGAAATCACAGTGAAGCATCCATTGGAGCATTCATGGACTTTTTG
GTTTGATAACCCTACCACTAAATCTCGACAAACTGCTTGGGGAAGCTCACTTCGAA
ATGTCTACACTTTCTCCACTGTTGAAGATTTTTGGGGTGCTTACAATAATATCCATC
ACCCAAGCAAGTTAATTATGGGAGCAGACTTTCATTGTTTTAAGCACAAAATTGAGC
CAAAGTGGGAAGATCCTGTATGTGCCAATGGAGGGACGTGGAAAATGAGTTTTTCG
AAGGGTAAATCTGATACCAGCTGGCTGTATACGCTGCTGGCAATGATTGGACATCA
ATTCGATCATGGAGATGAAATTTGTGGAGCAGTTGTTAGTGTCCGGGCTAAGGGAG
AAAAAATAGCTTTGTGGACCAAGAATGCTGCAAATGAAACAGCTCAGGTTAGCATT
GGTAAGCAATGGAAGCAGTTTCTAGATTACAGTGATTCGGTTGGCTTCATATTTCAC
GACGATGCAAAGAGGCTCGACAGAAATGCCAAGAATCGTTACACCGTATAGTTCTT
GATGCAGTGTGGGATTGCAAGAAACACAATTCGTACTGGAAAGGTTGGTAGGTACT
AGTTTAGTTTCTCATTTGATAAGCTTCTGGTTTGAGTAACTCGTGTGTTGGTGTTTA
CACTTTCTAATCGTGGAAAATTGTTTGATTTGAATCCATGCCTCTATGTTTCGTCAC
ATAACAAAACACAAAT

Figure 2: ELISA Values indicating amounts of virus accumulation for T1 plants of strain A127 26 days post CMV inoculation Figure 3: ELISA Values indicating amounts of virus accumulation for T1 plants of strain A127 20 days post CMV inoculation Figure 4: ELISA Values indicating amounts of virus accumulation for T1 plants of strains A132 and A143 30 days post CMV inoculation

Figure 6-1

| | | |
|---|---|---|
| LseIF4E03mRNA | TTGAGCCAAAGTGGGAAGATCCTGTATGTGCCAATGGAGGGACGTGGAAAATGAGTTTTTCGAAGGGTAAATCTGATA-CCAGCTGGCTGTATACGG | SEQ ID NO: 17 |
| A127-14-1-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-10-P | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-11-P | TTGAGCCAAAGTGGGAAGATCCTGTATGTGCCAATGGAGGGACGTGGAAAATGAGTTTTTCGAAGGGTAAATCTGATA----GCTGGCTGTATACGG | SEQ ID NO: 19 |
| A127-14-12-P | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-2-PR | TTGAGCCAAAGTGGGAAGATCCTGTATGTGCCAATGGAGGGACGTGGAAAATGAGTTTTTCGAAGGGTAAATCTGATA----GCTGGCTGTATACGG | SEQ ID NO: 19 |
| A127-14-4-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-5-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-6-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |
| A127-14-7-PR | TTGAGCCAAAGTGGGAAGATCCTGTATGTGCCAATGGAGGGACGTGGAAAATGAGTTTTTCGAAGGGTAAATCTGATA----GCTGGCTGTATACGG | SEQ ID NO: 19 |
| A127-14-8-PR | TTGAGCCAAAGTGGGAAGATCCTGTATGTGCCAATGGAGGGACGTGGAAAATGAGTTTTTCGAAGGGTAAATCTGATA----GCTGGCTGTATACGG | SEQ ID NO: 19 |
| A127-14-9-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 18 |

| | | |
|---|---|---|
| LseIF4E03mRNA | ATTGAGCCAAAGTGGGAAGATCCTGTATGTGCCAATGGAGGGACGTGGAAAATGAGTTTTTCGAAGGGTAAATCTGATACCAGCTGGCTGTATACGG | SEQ ID NO: 20 |
| A127-21-1-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-2-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-3-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-4-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-5-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-6-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-7-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |
| A127-21-8-PR | ATTGAGCCAAAGTGGGAAGATCCTGTATGTGCCAATGGAGGGACGTGGAAAATGAGTTTTTCGAAGGGTAAATCTGATA---GCTGGCTGTATACGG | SEQ ID NO: 21 |

| | | |
|---|---|---|
| LseIF4E03mRNA | TTGAGCCAAAGTGGGAAGATCCTGTATGTGCCAATGGAGGGACGTGGAAAATGAGTTTTTCGAAGGGTAAATCTGATA-CCAGCTGGCTGTATACGG | SEQ ID NO: 22 |
| A127-24-1-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-10-P | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-11-P | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-12-P | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-2-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-3-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-4-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-5-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-6-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-7-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-8-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |
| A127-24-9-PR | TTGAGCCAAAGTGGGAAGATCCTGTATGTGCCAATGGAGGGACGTGGAAAATGAGTTTTTCGAAGGGTAAATCTGATACCCAGCTGGCTGTATACGG | SEQ ID NO: 23 |

Figure 6-2

```
LseIF4E03mRNA TTGAGCCAAAGTGGGAAGATCCTGTATGTGCCAATGGAGGGACGTGGAAAATGAGTTTTTCGAAGGGTAAATCTGATACCAGCTGGCTGTATACGCT SEQ ID NO: 24
A132-1-2-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 25
A132-1-3-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 25
A132-1-6-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 25
A132-1-11-PR  TTGAGCCAAAGTGGGAAGATCCTGTATGTGCCAATGGAGGGACGTGGAAAATGAGTTTTTCGAAGGGTAA--C--A-----GCTGGCTGTATACGGT SEQ ID NO: 26
A132-1-12-PR  TTGAGCCAAAGTGGGAAGATCCTGTATGTGCCAATGGAGGGACGTGGAAAATGAGTTTTTCGAAGGGTAA--C--A-----GCTGGCTGTATACGGT SEQ ID NO: 26
A132-1-9-PRE  TTGAGCCAAAGTGGGAAGATCCTGTATGTGCCAATGGAGGGACGTGGAAAATGAGTTTTTCGAAGGGTAA--C--A-----GCTGGCTGTATACGGT SEQ ID NO: 26
A132-1-1-PRE  ATGAGCCAAAGTGGGAAGATCCAGTATGTGCCAATGGAGGGACGTGGAAAATGAGTTTTTGGAAGGGTAAATGTGATA---GCTGGCTGTATACGGT SEQ ID NO: 27
A132-1-8-PRE  CTGAGCCAAAGGGTGAAGATCCTGTCAGTGGCAAGGGAGGGAAATGGAAATTGAGTTTTTGGAAGTGTAA--C--A-----GCTGGCTGTATACGGT SEQ ID NO: 28
A132-1-10-PR  ACGAACCAAAGNGGGAAGATCAAGTTCGTGTCAATGGCGGGACGGGGAAAATGAATTTTTNGAAGGGTAAATGTAACA---GCTGGCTGTATACGGT SEQ ID NO: 29

LseIF4E03mRNA TTGAGCCAAAGTGGGAAGATCCTGTATGTGCCAATGGAGGGACGTGGAAAATGAGTTTTTCGAAGGGTAAATCTGATACCAGCTGGCTGTATACGCT SEQ ID NO: 30
A132-5-1-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-2-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-3-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-4-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-5-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-6-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-7-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
A132-5-8-PRE  TTGAGCCAAAGTGGGAAGATCCTGTATGTGCCAATGGAGGGACGTGGAAAATGAGTTTTTCGAAGGGTAAATCTGATA---GCTGGCTGTATACGGT SEQ ID NO: 31
```

Positive control: Wt inoculated with CMV Negative control: non-inoculated

CMV Resistance
Comparison of insect-mediated morbidities

| | Days post inoculation | |
|---|---|---|
| | 22dpi | 26dpi |
| A132-1-13 (13)* | 7% | 23% |
| Control (9)* | 33% | 44% |

*each number in () indicating the number of plants tested
dpi = days post inoculation

SEQUENCE LISTING

```
<160> NUMBER OF SEQ ID NOS: 31

<210> SEQ ID NO 1
<211> LENGTH: 916
<212> TYPE: DNA
<213> ORGANISM: Solanum lycopersicum

<400> SEQUENCE: 1

agtgctccac agtccacaga gcagcaaaaa tggcagcagc tgaaatggag agaacgatgt     60

cgtttgatgc agctgagaag ttgaaggccg ccgatggagg aggaggagag gtagacgatg    120

aacttgaaga aggtgaaatt gttgaagaat caaatgatac ggcatcgtat ttagggaaag    180

aaatcacagt gaagcatcca ttggagcatt catggacttt ttggtttgat aaccctacca    240

ctaaatctcg acaaactgct tggggaagct cacttcgaaa tgtctacact ttctccactg    300

ttgaagattt ttggggtgct tacaataata tccatcaccc aagcaagtta attatgggag    360

cagactttca ttgttttaag cacaaaattg agccaaagtg ggaagatcct gtatgtgcca    420
```

-continued

```
atggagggac gtggaaaatg agtttttcga agggtaaatc tgataccagc tggctgtata    480

cgctgctggc aatgattgga catcaattcg atcatggaga tgaaatttgt ggagcagttg    540

ttagtgtccg ggctaaggga gaaaaaatag ctttgtggac caagaatgct gcaaatgaaa    600

cagctcaggt tagcattggt aagcaatgga agcagtttct agattacagt gattcggttg    660

gcttcatatt tcacgacgat gcaaagaggc tcgacagaaa tgccaagaat cgttacaccg    720

tatagttctt gatgcagtgt gggattgcaa gaaacacaat tcgtactgga aaggttggta    780

ggtactagtt tagtttctca tttgataagc ttctggtttg agtaactcgt gtgttggtgt    840

ttacactttc taatcgtgga aaattgtttg atttgaatcc atgcctctat gtttcgtcac    900

ataacaaaac acaaat                                                    916
```

<210> SEQ ID NO 2
<211> LENGTH: 166
<212> TYPE: DNA
<213> ORGANISM: Solanum lycopersicum

<400> SEQUENCE: 2

```
tgcttacaat aatatccatc acccaagcaa gttaattatg ggagcagact ttcattgttt     60

taagcacaaa attgagccaa agtgggaaga tcctgtatgt gccaatggag ggacgtggaa    120

aatgagtttt tcgaagggta aatctgatac cagctggctg tatacg                   166
```

<210> SEQ ID NO 3
<211> LENGTH: 20
<212> TYPE: DNA
<213> ORGANISM: Solanum lycopersicum

<400> SEQUENCE: 3

```
agggtaaatc tgataccagc                                                 20
```

<210> SEQ ID NO 4
<211> LENGTH: 21
<212> TYPE: DNA
<213> ORGANISM: Artificial sequence
<220> FEATURE:
<223> OTHER INFORMATION: variant

<400> SEQUENCE: 4

```
agggtaaatc tgatacccag c                                               21
```

<210> SEQ ID NO 5
<211> LENGTH: 17
<212> TYPE: DNA
<213> ORGANISM: Artificial sequence
<220> FEATURE:
<223> OTHER INFORMATION: variant

<400> SEQUENCE: 5

```
agggtaaatc tgatagc                                                    17
```

<210> SEQ ID NO 6
<211> LENGTH: 11
<212> TYPE: DNA
<213> ORGANISM: Artificial sequence
<220> FEATURE:
<223> OTHER INFORMATION: variant

<400> SEQUENCE: 6

```
agggtaacag c                                                          11
```

-continued

<210> SEQ ID NO 7
<211> LENGTH: 17
<212> TYPE: DNA
<213> ORGANISM: Artificial sequence
<220> FEATURE:
<223> OTHER INFORMATION: variant

<400> SEQUENCE: 7
agggtaaatg tgatagc 17

<210> SEQ ID NO 8
<211> LENGTH: 11
<212> TYPE: DNA
<213> ORGANISM: Artificial sequence
<220> FEATURE:
<223> OTHER INFORMATION: variant

<400> SEQUENCE: 8
agtgtaacag c 11

<210> SEQ ID NO 9
<211> LENGTH: 17
<212> TYPE: DNA
<213> ORGANISM: Artificial sequence
<220> FEATURE:
<223> OTHER INFORMATION: variant

<400> SEQUENCE: 9
agggtaaatg taacagc 17

<210> SEQ ID NO 10
<211> LENGTH: 20
<212> TYPE: DNA
<213> ORGANISM: Solanum lycopersicum

<400> SEQUENCE: 10
ggccaccgaa gcaccggtag 20

<210> SEQ ID NO 11
<211> LENGTH: 24
<212> TYPE: DNA
<213> ORGANISM: Artificial sequence
<220> FEATURE:
<223> OTHER INFORMATION: primer 1

<400> SEQUENCE: 11
atccatcacc caagcaagtt aatt 24

<210> SEQ ID NO 12
<211> LENGTH: 24
<212> TYPE: DNA
<213> ORGANISM: Artificial sequence
<220> FEATURE:
<223> OTHER INFORMATION: primer 2

<400> SEQUENCE: 12
gtccacaaag ctattttttc tccc 24

<210> SEQ ID NO 13
<211> LENGTH: 28
<212> TYPE: DNA
<213> ORGANISM: Artificial sequence
<220> FEATURE:
<223> OTHER INFORMATION: primer 3

<400> SEQUENCE: 13

-continued ccgtcgtgaa aaagctatac aaaaggag 28

<210> SEQ ID NO 14
<211> LENGTH: 22
<212> TYPE: DNA
<213> ORGANISM: Artificial sequence
<220> FEATURE:
<223> OTHER INFORMATION: primer 4

<400> SEQUENCE: 14
gcttttcgaa gagaacttcc cc 22

<210> SEQ ID NO 15
<211> LENGTH: 22
<212> TYPE: DNA
<213> ORGANISM: Artificial sequence
<220> FEATURE:
<223> OTHER INFORMATION: primer 5

<400> SEQUENCE: 15
gtacagagtt cagggttgag cg 22

<210> SEQ ID NO 16
<211> LENGTH: 23
<212> TYPE: DNA
<213> ORGANISM: Artificial sequence
<220> FEATURE:
<223> OTHER INFORMATION: primer 6

<400> SEQUENCE: 16
agcaatactg ccaactcagc tcc 23

<210> SEQ ID NO 17
<211> LENGTH: 96
<212> TYPE: DNA
<213> ORGANISM: Solanum lycopersicum

<400> SEQUENCE: 17
ttgagccaaa gtgggaagat cctgtatgtg ccaatggagg gacgtggaaa atgagttttt 60
cgaagggtaa atctgatacc agctggctgt atacgc 96

<210> SEQ ID NO 18
<211> LENGTH: 97
<212> TYPE: DNA
<213> ORGANISM: Solanum lycopersicum

<400> SEQUENCE: 18
ttgagccaaa gtgggaagat cctgtatgtg ccaatggagg gacgtggaaa atgagttttt 60
cgaagggtaa atctgatacc cagctggctg tatacgg 97

<210> SEQ ID NO 19
<211> LENGTH: 93
<212> TYPE: DNA
<213> ORGANISM: Solanum lycopersicum

<400> SEQUENCE: 19
ttgagccaaa gtgggaagat cctgtatgtg ccaatggagg gacgtggaaa atgagttttt 60
cgaagggtaa atctgatagc tggctgtata cgg 93

<210> SEQ ID NO 20
<211> LENGTH: 97
<212> TYPE: DNA

-continued

<213> ORGANISM: Solanum lycopersicum

<400> SEQUENCE: 20
attgagccaa agtgggaaga tcctgtatgt gccaatggag ggacgtggaa aatgagtttt 60
tcgaagggta aatctgatac cagctggctg tatacgc 97

<210> SEQ ID NO 21
<211> LENGTH: 94
<212> TYPE: DNA
<213> ORGANISM: Solanum lycopersicum

<400> SEQUENCE: 21
attgagccaa agtgggaaga tcctgtatgt gccaatggag ggacgtggaa aatgagtttt 60
tcgaagggta aatctgatag ctggctgtat acgg 94

<210> SEQ ID NO 22
<211> LENGTH: 96
<212> TYPE: DNA
<213> ORGANISM: Solanum lycopersicum

<400> SEQUENCE: 22
ttgagccaaa gtgggaagat cctgtatgtg ccaatggagg gacgtggaaa atgagttttt 60
cgaagggtaa atctgatacc agctggctgt atacgc 96

<210> SEQ ID NO 23
<211> LENGTH: 97
<212> TYPE: DNA
<213> ORGANISM: Solanum lycopersicum

<400> SEQUENCE: 23
ttgagccaaa gtgggaagat cctgtatgtg ccaatggagg gacgtggaaa atgagttttt 60
cgaagggtaa atctgatacc cagctggctg tatacgg 97

<210> SEQ ID NO 24
<211> LENGTH: 97
<212> TYPE: DNA
<213> ORGANISM: Solanum lycopersicum

<400> SEQUENCE: 24
ttgagccaaa gtgggaagat cctgtatgtg ccaatggagg gacgtggaaa atgagttttt 60
cgaagggtaa atctgatacc agctggctgt atacgct 97

<210> SEQ ID NO 25
<211> LENGTH: 94
<212> TYPE: DNA
<213> ORGANISM: Solanum lycopersicum

<400> SEQUENCE: 25
ttgagccaaa gtgggaagat cctgtatgtg ccaatggagg gacgtggaaa atgagttttt 60
cgaagggtaa atctgatagc tggctgtata cggt 94

<210> SEQ ID NO 26
<211> LENGTH: 88
<212> TYPE: DNA
<213> ORGANISM: Solanum lycopersicum

<400> SEQUENCE: 26
ttgagccaaa gtgggaagat cctgtatgtg ccaatggagg gacgtggaaa atgagttttt 60
cgaagggtaa cagctggctg tatacggt 88

-continued

<210> SEQ ID NO 27
<211> LENGTH: 94
<212> TYPE: DNA
<213> ORGANISM: Solanum lycopersicum

<400> SEQUENCE: 27
atgagccaaa gtgggaagat ccagtatgtg ccaatggagg gacgtggaaa atgagttttt 60
ggaagggtaa atgtgatagc tggctgtata cggt 94

<210> SEQ ID NO 28
<211> LENGTH: 88
<212> TYPE: DNA
<213> ORGANISM: Solanum lycopersicum

<400> SEQUENCE: 28
ctgagccaaa gggtgaagat cctgtcagtg gcaagggagg gaaatggaaa ttgagttttt 60
ggaagtgtaa cagctggctg tatacggt 88

<210> SEQ ID NO 29
<211> LENGTH: 94
<212> TYPE: DNA
<213> ORGANISM: Solanum lycopersicum
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 29
acgaaccaaa gngggaagat caagttcgtg tcaatggcgg gacggggaaa atgaattttt 60
ngaagggtaa atgtaacagc tggctgtata cggt 94

<210> SEQ ID NO 30
<211> LENGTH: 97
<212> TYPE: DNA
<213> ORGANISM: Solanum lycopersicum

<400> SEQUENCE: 30
ttgagccaaa gtgggaagat cctgtatgtg ccaatggagg gacgtggaaa atgagttttt 60
cgaagggtaa atctgatacc agctggctgt atacgct 97

<210> SEQ ID NO 31
<211> LENGTH: 94
<212> TYPE: DNA
<213> ORGANISM: Solanum lycopersicum

<400> SEQUENCE: 31
ttgagccaaa gtgggaagat cctgtatgtg ccaatggagg gacgtggaaa atgagttttt 60
cgaagggtaa atctgatagc tggctgtata cggt 94

VIRUS-RESISTANT PLANT AND METHOD FOR PRODUCING THE SAME

REFERENCE TO A SEQUENCE LISTING SUBMITTED VIA EFS-WEB

The content of the ASCII text file of the sequence listing named "20210628_101278_001US1_ST25" which is 8.02 kb in size was created on Jun. 28, 2021 and electronically submitted via EFS-Web herewith the application is incorporated herein by reference in its entirety.

TECHNICAL FIELD

The present invention relates to a plant virus-resistant plant, in particular, to a Cucumber mosaic virus (CMV)-resistant plant belonging to the family Solanaceae. The present invention also relates to a method for producing such a virus-resistant plant.

BACKGROUND ART

Cucumber mosaic virus (hereinafter, referred to as CMV) is one of plant viruses that cause serious diseases to many crops including solanaceous crops such as tomato (*Solanum lycopersicum*) and cucumber (*Cucumis sativas* L.). CMV propagates primarily via aphids, and infect 1000 or more plant species and crops, economically damaging important agricultural products in the temperate, subtropical, and tropical regions in the world. When CMV infects with the crops, the virus propagates at the site of infection, and then spreads to the whole plant body via the vascular bundles, in particular the sieve tube, and causes symptoms of mosaic, yellowing, fern leaf, stunt, necrosis, and so on, decreasing quality and yields of fruits and leaves. For example, it has been reported that in 1987 CMV suddenly appeared in leading tomato-producing areas in Italy and Spain to damage almost all the tomato fruits, and the areas fell into a catastrophic situation. In Indonesia and South Korea, similarly, it has been recorded that chili pepper and bell pepper were significantly damaged by CMV. Also, in Japan, such case occasionally occurs in areas with unexpectedly poor pest control.

While CMV infects a wide variety of crops and causes economic damage as described, there are not many methods for protecting crops from infection by CMV. Microbicides and the like are ineffective to most plant viruses. Examples of pest control methods for most common plant viruses including CMV are hindering intrusion of insect vectors such as aphids by using an insect-proof net or the like, and killing insects with agrochemicals or the like; however, it is difficult to completely prevent viral diseases.

Genes of hosts are involved in infection by plant viruses, and not only genetically predominant virus resistance (e.g., an N gene that is isolated from tobacco and prevents spread of infection by tobacco mosaic virus), but also virus resistance that is recessively inherited has been found. A representative example of this phenomenon is the relation between viruses belonging to the family Potyviridae and corresponding resistance genes, the eIF4E family (e.g., eIF4E, eIF(iso)4E). There are a huge number of viruses belonging to the family Potyviridae, as Potyvirus infects various kind of plants and subdivide. On the other hand, eIF4E, one of eukaryotic translation initiation factors, is a translation initiation factor of a host. For example, Turnip mosaic virus, which belongs to the family Potyviridae, utilizes a translation initiation factor of a host plant for the purpose of binding a plant ribosome to viral RNA in order to translate various viral proteins such as RNA-dependent RNA polymerase to copy itself. Moreover, eIF4E is known to be required for replication and cell-to-cell transfer of viruses. Accordingly, defect in this host translation gene can affect virus resistance.

Previously reported is that mutation of an eIF4E family gene actually led to acquisition of resistance to viruses belonging to the family Potyviridae in *Arabidopsis thaliana* as a model plant, and the genus *Nicotiana*, tomato, and chili pepper, which belong to the family Solanaceae (e.g., Non Patent Literatures 1 and 2). However, resistance to CMV has been still confirmed only for *Arabidopsis thaliana*, and has not been found for other plants including tomato. In particular, Non Patent Literature 1, which relates to Potyvirus infection in tomato and knockdown of eIF4E1 and eIF4E2, discloses that the involvement of eIF4E in the viral infectious cycle appears to be restricted to potyviruses, as infection by viruses not belonging to the family Potyviridae, such as CMV, is not impaired in transgenic lines silenced for eIF4E or eIF(iso)4E (e.g., Non Patent Literature 1, p. 4, left column, lines 12 to 15). It has been also reported that when a mutation that leads to complete loss of the function of eIF4E was introduced into cucumber, resistance to CVYV (Cucumber vein yellowing virus), ZYMV (Zucchini yellow mosaic virus), and PRSV (Papaya ring spot mosaic virus) was imparted but resistant to CMV was not imparted (Non Patent Literature 3, in particular, Table 2).

CITATION LIST

Non Patent Literature

Non Patent Literature 1: Mazier et al. (2011) PLOS ONE 6: e29595

Non Patent Literature 2: Sato et al. (2005) FEBS Lett. 579(5): 1167-1171.

Non Patent Literature 3: J. Chandrasekaran et al., (2016) Molecular Plant Pathology, 17(7): 1140-1153

SUMMARY OF INVENTION

Technical Problem

Virus resistance expected to be imparted by suppression of an eIF4E family gene varies among homologs of the gene, and among host plants. In most cases, the virus resistance is against plant viruses belonging to the family Potyviridae, and that found for tomato is only against Potato virus Y (PVY), Pepper mottle virus (PepMoV), Tobacco etch virus (TEV), and so on. Meanwhile, resistance to CMV, which is a virus belonging to different family, has not been found. CMV is an RNA virus, which is a common feature with viruses belonging to the family Potyviridae, but the gene configuration is largely different, and the form of the genome RNA is also different from that of Potyvirus. While viruses belonging to the family Potyviridae are composed of a single genome, CMV is composed of a three-segmented genome, and each segment forms a virus particle, and CMV infects and proliferates in the set of all the particles or segments. Despite that diseases caused by CMV are important diseases that present severe symptoms, almost no resistance genes, including resistance genes for translation initiation factors, have been currently found for crops, and completely no resistance gene has been found for the family Solanaceae. For this reason, CMV has been prevented only by the prevention of aphids as the insect vector, and production of resistant varieties has been desired in the site of plant breeding.

In the above-described circumstances, an object of the present invention is to provide a CMV-resistant solanaceous plant and a method for producing the plant, a mutated gene for production of a CMV-resistant solanaceous plant, and use of them.

Solution to Problem

The present inventors diligently studied to achieve the object, and as a result, produced a plant having a mutation at a specific site of a specific homolog of eIF4E of tomato, a solanaceous plant. When CMV was inoculated into the produced plants, the plants were found to have CMV resistance for a long period of time, and thus the present invention was completed. This is the first report of a CMV-resistant plant in the family Solanaceae.

Specifically, the present invention relates to the following.

[1]

A cucumber mosaic virus (CMV)-resistant solanaceous plant having a mutated eIF4E gene encoding an eIF4E protein nonfunctional for CMV.

[2]

The CMV-resistant solanaceous plant according to [1], wherein the plant belongs to the genus *Solanum.*

[3]

The CMV-resistant plant according to [1] or [2], wherein the plant is tomato, and the mutated eIF4E gene is an eIF4E gene on chromosome 3 of tomato.

[4]

The CMV-resistant plant according to any one of [1] to [3], wherein the mutated eIF4E gene has one or more mutations selected from the following mutations:

(a) a frameshift mutation;

(b) a nonsense mutation;

(c) deletion of continuous or noncontinuous 3n nucleotides (n=1 to 7); and (d) substitution, deletion, addition, and/or insertion of one or more nucleotides, in the nucleotide sequence of exon 2.

[5]

The CMV-resistant plant according to any one of [1] to [4], wherein:

the plant is tomato, and the mutated eIF4E gene has a mutation selected from the group consisting of: insertion of one nucleotide; deletion of three nucleotides; and deletion of nine nucleotides, in the nucleotide sequence (SEQ ID NO: 2) of exon 2 of an eIF4E gene on chromosome 3 of tomato.

[6]

The CMV-resistant plant according to any one of [1] to [4], wherein:

the plant is tomato, and the mutated eIF4E gene has a mutation selected from the group consisting of: insertion of one nucleotide between the nucleotides at positions 15 and 16; deletion of the three nucleotides at positions 16 to 18; and deletion of any nine nucleotides of the nucleotides at positions 8 to 18, in the nucleotide sequence AGGGTAAATCTGATACCAGC (SEQ ID NO: 3) in exon 2 of an eIF4E gene on chromosome 3 of tomato.

[7]

A method for producing a cucumber mosaic virus (CMV)-resistant plant, the method comprising mutating an eIF4E gene of a solanaceous plant into a mutated eIF4E gene encoding an eIF4E protein nonfunctional for CMV.

[8]

The method for producing a CMV-resistant plant according to [7], wherein:

the plant is tomato, and the mutating is a mutating an eIF4E gene on chromosome 3 of tomato.

[9]

The method for producing a CMV-resistant plant according to [7] or [8], wherein the mutating is introducing one or more mutations selected from the following mutations:

(a) a frameshift mutation;

(b) a nonsense mutation;

(c) deletion of continuous or noncontinuous 3n nucleotides (n=1 to 7); and (d) substitution, deletion, addition, and/or insertion of one or more nucleotides, in the nucleotide sequence of exon 2 of the eIF4E gene.

The present invention also relates to the following.

[10]

A processed product of the CMV-resistant plant according to any one of [1] to [4].

[11]

A method for producing a processed product of a cucumber mosaic virus (CMV)-resistant plant, the method comprising mutating an eIF4E gene of a solanaceous plant into a mutated eIF4E gene encoding an eIF4E protein nonfunctional for CMV.

[12]

The method for producing a processed product according to [11], wherein the plant is tomato, and the mutating is mutating an eIF4E gene on chromosome 3 of tomato.

[13]

The method for producing a processed product according to [11] or [12], wherein the mutating is introducing one or more mutations selected from the following mutations:

(a) a frameshift mutation;

(b) a nonsense mutation;

(c) deletion of continuous or noncontinuous 3n nucleotides (n=1 to 7); and (d) substitution, deletion, addition, and/or insertion of one or more nucleotides, in the nucleotide sequence of exon 2 of the eIF4E gene.

Further, the present invention relates to the following.

[14]

A mutated eIF4E gene encoding an eIF4E protein nonfunctional for cucumber mosaic virus (CMV).

[15]

The mutated eIF4E gene according to [14], derived from a solanaceous plant.

[16]

The mutated eIF4E gene according to [14] or [15], derived from an eIF4E gene on chromosome 3 of tomato.

[17]

The mutated eIF4E gene according to any one of [14] to [16], having one or more mutations selected from the following mutations:

(a) a frameshift mutation;

(b) a nonsense mutation;

(c) deletion of continuous or noncontinuous 3n nucleotides (n=1 to 7); and (d) substitution, deletion, addition, and/or insertion of one or more nucleotides, in the nucleotide sequence of exon 2.

[18]

The mutated eIF4E gene according to any one of [14] to [17], derived from tomato, and having a mutation selected from the group consisting of: insertion of one nucleotide; deletion of three nucleotides; and deletion of nine nucleotides, in the nucleotide sequence (SEQ ID NO: 2) of exon 2 of an eIF4E gene on chromosome 3 of tomato.

[19]

The mutated eIF4E gene according to any one of [14] to [18], derived from tomato, and having a mutation selected from the group consisting of: insertion of one nucleotide between the nucleotides at positions 15 and 16; deletion of the three nucleotides at positions 16 to 18; and deletion of any nine nucleotides of the nucleotides at positions 8 to 18, in the nucleotide sequence AGGGTAAATCTGATACCAGC (SEQ ID NO: 3) in exon 2 of an eIF4E gene on chromosome 3 of tomato.

[20]

Use of the mutated eIF4E gene according to any one of [14] to [19] in production of a CMV-resistant solanaceous plant.

[21]

Use of the CMV-resistant solanaceous plant according to any one of [1] to [6] in production of a processed product of a solanaceous plant.

[22]

A plant cell of a solanaceous plant, the cell having the mutated eIF4E gene according to any one of [14] to [19].

[23]

A method for producing a plant cell of the CMV-resistant solanaceous plant according to any one of [1] to [6].

[24]

A method for producing a seed of the CMV-resistant solanaceous plant according to any one of [1] to [6].

[25]

Use of the mutated eIF4E gene according to any one of [14] to [19] in production of a seed of a CMV-resistant solanaceous plant.

[26]

A vector, promoter, or kit comprising the mutated eIF4E gene according to any one of [14] to [19].

[27]

Use of the vector, promoter, or kit according to [26] in production of a CMV-resistant solanaceous plant, a plant cell of the plant, a seed of the plant, or a progeny of the plant.

Advantageous Effects of Invention

According the present invention, a CMV-resistant solanaceous plant and a method for producing the plant, a mutated gene for production of a CMV-resistant solanaceous plant and their use can be provided.

BRIEF DESCRIPTION OF DRAWINGS

FIG. 1 shows a nucleotide sequence corresponding to the mRNA sequence of eIF4E present on chromosome 3 of a wild-type plant of tomato (SEQ ID NO: 1). In the actual RNA, T (thymine) in the figure is U (uracil). The portion indicated by a wavy line (166 nucleotides) is the nucleotide sequence of exon 2 (SEQ ID NO: 2), and the hatched portion is a target site for editing (SEQ ID NO: 3). The upstream of the nucleotide (A) present at the third before TGG (PAM sequence) in the rectangular frame in the figure is edited.

FIG. 5*a*: A127-8 with no symptom. FIG. 5*b*: A127-2, for which mosaic, yellowing, and fern leaf symptoms are observed.

FIG. 6-1 shows results of sequence analysis for a part around an edited site in an eIF4E gene present on chromosome 3 of each T1 plant of A127-14, A127-21, and A127-24. The top in each sequence group is the sequence of wild-type (WT). The overlined part in the figure is the target site for editing, and a nucleotide enclosed by a rectangle indicates a mutation from the wild-type.

FIG. 6-2 shows results of sequence analysis for a part around an edited site in an eIF4E gene present on chromosome 3 of each T1 plant of A132-1 and A132-5. The top in each sequence group is the sequence of wild-type (WT). The overlined part in the figure is the target site for editing, and a nucleotide enclosed by a rectangle indicates a mutation from the wild-type.

FIG. 9-1 shows a graph for comparison of morbidity determined by visual observation and ELISA between T2 generations from A132-5 and A127-24 and a wild-type control in Example 6. Because plants for which onset was found were all ELISA-positive, only an incidence was shown when the incidence was identical to the corresponding virus infection rate.

FIG. 9-2 shows results of measurement of degrees of virus accumulation by ELISA for T2 generations from some plants in Example 6.

FIG. 10 shows results of aphid-inoculation with CMV in Example 7 for T2 generations to determine CMV resistance.

DESCRIPTION OF EMBODIMENTS

Figure 2:
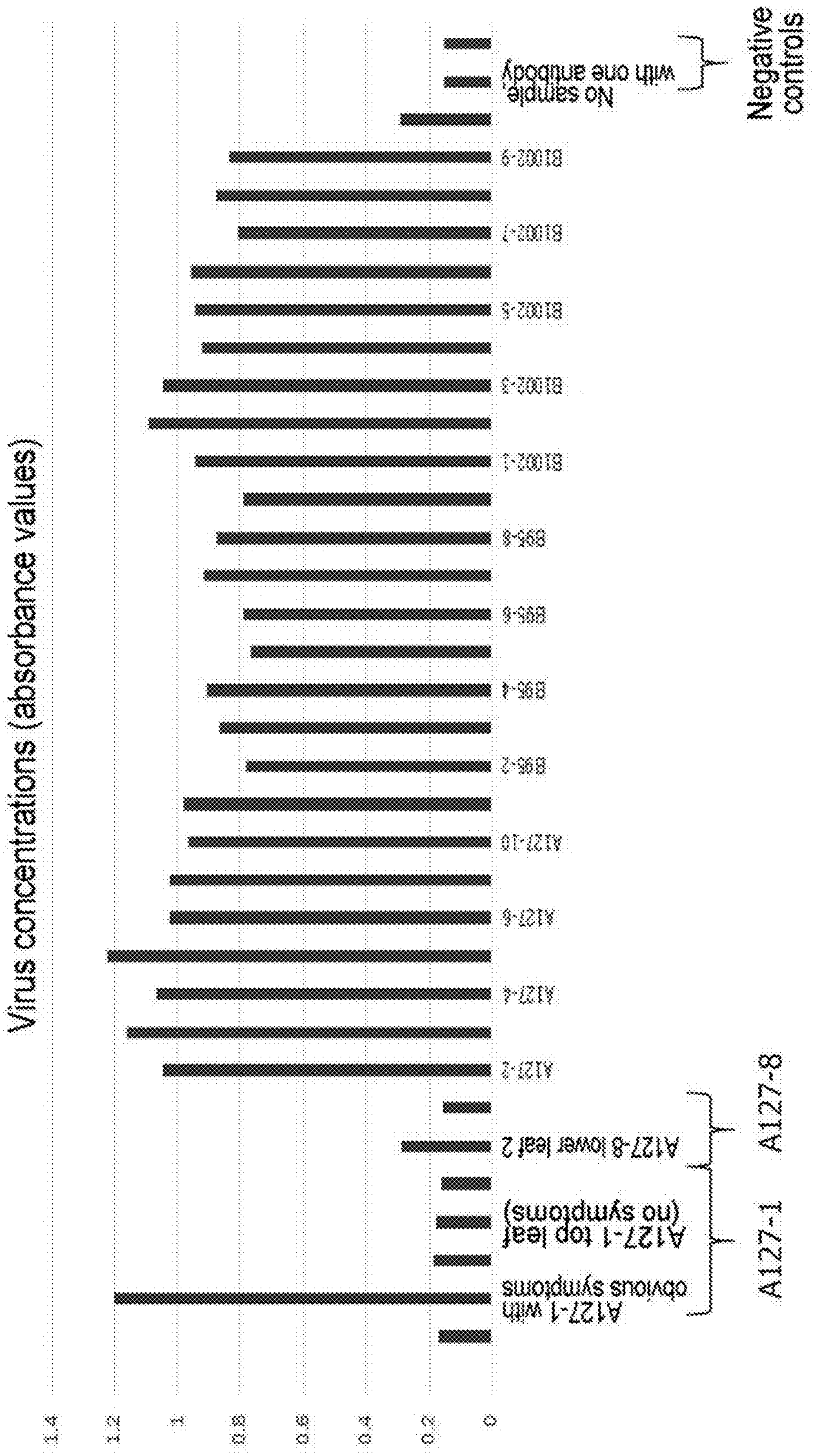
FIG. 2 shows a graph showing amounts of virus accumulation for six plants of the strain A127, four plants of the strain B95, and five plants of the strain B100 (each being a T1 plant) 26 days after CMV inoculation. Samples were obtained from four positions for A127-1, and from two positions for the others. ELISA values (absorbance values) were measured for the samples with an anti-CMV antibody, and A127-1 and A127-8 were found to have CMV resistance.

Hereinafter, embodiments to implement the present invention (hereinafter, also referred to as "the present embodiments") will be described in detail. The present invention is not limited to the following present embodiments and the drawings, and can be implemented with various modifications without departing from the scope of the invention.

In one aspect, the present embodiments relate to a CMV-resistant solanaceous plant. The CMV-resistant plant in the present embodiments refers to a plant having a characteristic to suppress the proliferation of CMV after infection and/or a characteristic to suppress the development of symptoms of CMV infection.

CMV, an RNA virus, is composed of a three-segmented genome, and each segment forms a virus particle, and CMV infects and proliferates in the set of all the particles or segments. Upon infecting a plant, CMV utilizes the translation initiation factor eIF4E of a genome of the plant as a host to bind a cap structure of an RNA terminus of CMV to eIF4E, thereby initiating translation of viral movement protein. CMV is largely different from Potyvirus and so on in that CMV has, similarly to mRNA of animals and plants, a cap structure at the 5'-end of the viral genomic RNA, whereas Potyvirus and so on include the protein VPg linked to the 5'-end of the viral genomic RNA. Viruses with VPg exhibit high affinity between VPg and plant eIF4E, and VPg strongly binds to plant eIF4E and the viral genes utilize the plant translation system, whereas CMV is considered to use an infection mechanism different from those of such viruses with VPg.

Whether a plant is CMV-resistance can be determined, for example, in a manner as described later in Examples. That is, a plant is infected with CMV by using a conventional method, and the accumulation of CMV in the plant body is examined by using a known technique such as an ELISA method and PCR. In addition, determination can be made by examining the presence or absence of any symptom of CMV infection (e.g., mosaic, yellowing, fern leaf, stunt, necrosis) in a plant infected with CMV. Multiple strains of CMV have been known, including the strains CMV-Y, CMV-O, CMV-Fny, and CMV-Nt9. It has been known that symptoms of CMV infection in plants can vary among strains, and hence the presence or absence of a symptom can be examined according to a CMV strain to infect. In one aspect, the CMV-resistant plant of the present embodiments is a plant with a reduced accumulation of CMV in the plant body, and/or a plant with alleviated symptoms of CMV infection when being infected with CMV, as compared with plants without a mutated eIF4E gene described later. In one aspect, the CMV-resistant plant of the present embodiments is such a plant that the accumulation of CMV in the plant body is comparable to that in a plant without CMV inoculation, and/or a plant for which no symptom of CMV infection is found, even 20 days or more after CMV infection.

As long as exhibiting CMV resistance, the CMV-resistant plant in the present embodiments may be any multiple-resistant plant that exhibits resistance to other viruses and bacteria, such as all species of Potyvirus that infect the family Solanaceae (e.g., PVY); viruses belonging to the genera *Bymovirus* and *Sobemovirus*, which have been reported to include, similarly to PVY, VPg at the 5'-end of the viral genome and have resistance due to a mutated translation initiation factor; viruses belonging to the genus *Carmovirus*, which have been reported to have resistance due to a mutated translation initiation factor; and viruses belonging to the family Geminiviridae (e.g., tomato yellow leaf curl virus (TYLCV)), which have not been reported yet to have resistance due to a mutated translation initiation factor, but cause enormous damage to production of crops including tomato.

In the present embodiments, the CMV-resistant plant is a plant belonging to the family Solanaceae, which is not limited to a particular plant and may be any one belonging to the family Solanaceae. The examples thereof include plants belonging to the genera *Solanum, Nicotiana*, and *Capsicum*, more specifically, tomato, eggplant, tobacco, chili pepper, and potato. In one aspect, the CMV-resistant plant of the present embodiments is preferably a plant belonging to the genus *Solanum*, more preferably tomato, eggplant, or potato, and particularly preferably tomato.

In one aspect, the present embodiment can be a part of the CMV-resistant plant, and more specifically, for example, it can be organs such as fruits, shoots, stems, roots, young branches, and anthers, plant tissue, pollens, and seeds. In one aspect, the present embodiments also relate to a method for producing such a plant or a part thereof, and use of a mutated eIF4E gene of the present embodiments in production of such a plant or a part thereof.

In one aspect, the CMV-resistant plant in the present embodiments can be made into a processed product, for example, for foods. That is, the present embodiments also relate to a processed product of a CMV-resistant solanaceous plant having a mutated eIF4E gene encoding an eIF4E protein nonfunctional for CMV. Further, the present embodiments relate to a method for producing a processed product of a CMV-resistant plant, the method comprising mutating an eIF4E gene of a solanaceous plant into a mutated eIF4E gene encoding an eIF4E protein nonfunctional for CMV.

The processed product is not limited to a particular product, and may be any processed product, depending on the type of the plant, for example, for foods or medical use. In the case that the CMV-resistant plant is tomato, for example, examples of processed products of tomato for foods include canned tomato, tomato paste, ketchup, tomato sauce, tomato soup, dried tomato, tomato juice, tomato powder, tomato concentrate, and dietary supplements produced from tomato as a raw material. Production of a processed product can be carried out by using a method known to those skilled in the art with a CMV-resistant plant as a raw material.

As long as being a plant that exhibits CMV resistance, the CMV-resistant plant in the present embodiments may be a scion, a rootstock, or the like for use in grafting. In one aspect, the present embodiments also relate to a plant cell (including a callus) or the like that is capable of regenerating the above-described CMV-resistant plant, and the plant cell has, similarly to the CMV-resistant plant in the present embodiments, a mutated eIF4E gene encoding an eIF4E protein nonfunctional for CMV. The present embodiments include plants obtained from such a plant cell as the CMV-resistant plant. In one aspect, the present embodiments also relate to a method for producing such a plant cell, and use of a mutated eIF4E gene of the present embodiments in production of such a plant cell.

The CMV-resistant plant in the present embodiments has a mutated eIF4E gene encoding an eIF4E protein nonfunctional for CMV (hereinafter, also referred to as a "CMV-resistant gene"). In one aspect, the present embodiments also relate to such a mutated eIF4E gene; a vector, promoter, or kit including such a mutated eIF4E gene; and use of such a vector, promoter, or kit in producing a CMV-resistant solanaceous plant, a plant cell thereof, a part of the plant (e.g., a seed), or a progeny thereof.

eIF4E is one of translation initiation factors in eukaryotes, and plays a key role in initiation of protein synthesis. eIF4E, together with eIF(iso)4E, constitutes the eIF4E family, and solanaceous plants are believed to have multiple isoforms of eIF4E. For example, tomato is known to have two isoforms of eIF4E, which are present on chromosome 2 and chromosome 3. It is known that one isoform of eIF(iso)4E is present in tomato, and it is present on chromosome 9. Further, chili pepper is known to have pvr1 and pvr2 present on chromosome 4 as genes homologous with eIF4E of tomato (pvr1 and pvr2 are alleles), and prv6 present on chromosome 3 is known as a gene homologous with eIF(iso)4E of tomato. Among these genes, eIF4E or a gene encoding a protein homologous therewith is preferably nonfunctional for CMV.

In the present embodiments, the eIF4E protein nonfunctional for CMV refers to an eIF4E protein that is unavailable for CMV to infect plants and proliferate or that reduces the infection and proliferation of CMV. In one aspect the CMV-resistant gene may be mutated so as not to encode a protein. Without being bound by any theory, the following mechanism is contemplated: upon infecting a plant, CMV uses a specific isoform of eIF4E among multiple isoforms present in solanaceous plants; if a gene encoding this specific isoform (eIF4E functional to CMV) is mutated to encode an eIF4E protein nonfunctional for CMV, translation of proteins that are encoded on the virus genome and required for infection and proliferation does not proceed, or CMV proteins that need interaction with eIF4E fail to function; hence, any one or more of CMV infection, CMV proliferation, and the development of symptoms of CMV infection are inhibited, which makes the plant a CMV-resistant plant. On the other hand, even if one of multiple eIF4E homologs present in a solanaceous plant has been mutated, the plant itself can use the other homologs, or the plant itself can use in some cases an eIF4E protein nonfunctional for CMV, and hence CMV resistance is expected to be successfully imparted without affecting the growth of the solanaceous plant as a host.

In one aspect, genes encoding an eIF4E protein functional to CMV have been all mutated in the CMV-resistant plant in the present embodiments. In the case of a polypoid plant such as an amphidiploid, for example, it is preferable that multiple genes encoding an eIF4E protein functional to CMV have been each mutated to a CMV-resistant gene. Such a CMV-resistant plant may have another normal eIF4E gene, as long as genes encoding an eIF4E protein functional to CMV have been mutated. Alternatively, an exogeneous CMV-resistant gene may be introduced, for example, to delete or disrupt all endogenous genes encoding an eIF4E protein functional to CMV.

In one aspect, the CMV-resistant gene in the present embodiments is a gene including a mutation in the nucleotide sequence of an eIF4E gene of a solanaceous plant functional to CMV, and preferably a gene including a mutation in the nucleotide sequence of exon 2 of the eIF4E gene. More specifically, in the case that the solanaceous plant is tomato, the CMV-resistant gene has a mutation in an eIF4E gene on chromosome 3 of tomato, preferably includes a mutation in the nucleotide sequence (SEQ ID NO: 2) of exon 2 thereof, and more preferably includes a mutation in the nucleotide sequence AGGGTAAATCTGATACCAGC (SEQ ID NO: 3) in the exon 2.

In one aspect, the CMV-resistant gene of the present embodiments includes one or more mutations selected from the following mutations:

(a) a frameshift mutation;
(b) a nonsense mutation;
(c) deletion of continuous or noncontinuous 3n nucleotides (n=1 to 7); and
(d) substitution, deletion, addition, and/or insertion of one or more nucleotides, in the nucleotide sequence of exon 2 of the eIF4E gene.

(a) A frameshift mutation is such a mutation that deletion or insertion of a nucleotide shifts reading frames for codons and as a result the codons encode a different amino acid sequence, thereby making the gene a CMV-resistant gene.
(b) A nonsense mutation is such a mutation that a codon originally encoding an amino acid becomes a stop codon, thereby making the gene a CMV-resistant gene.
(c) Deletion of continuous or noncontinuous 3n nucleotides (n=1 to 7, preferably n=1 to 3, for example, three, six, or nine nucleotides, more preferably n=3, for example, nine nucleotides) slightly alters amino acids encoded by nucleotides in the downstream of the deleted region, thereby making the gene a CMV-resistant gene.
(d) Substitution, deletion, addition, and/or insertion of one or more nucleotides changes reading frames for amino acids encoded by nucleotides in the downstream of the mutated region. Thereby, for example, the eIF4E protein is disrupted or the structure thereof is altered, which makes the gene a CMV-resistant gene. In one aspect, the mutation is preferably a mutation of a nucleotide other than the third nucleotide of a codon. In the present embodiments, the number of nucleotides substituted, deleted, added, and/or inserted is not limited to a particular number and may be any number that gives a CMV-resistant gene, and can be, for example, one to five, one to three, one or two, or one.

The above mutations (a) to (d) do not always exclusively occur, and, for example, the mutation (c) or (d) can result in the occurrence of the mutation (a) or (b).

In one aspect, the CMV-resistant gene of the present embodiments preferably includes any one or more of: deletion of continuous or noncontinuous nine nucleotides; deletion of continuous or noncontinuous three nucleotides; and a frameshift mutation by insertion of one nucleotide.

In one aspect, the mutated eIF4E gene has a mutation selected from the group consisting of: insertion of one nucleotide; deletion of three nucleotides; and deletion of nine nucleotides, in the nucleotide sequence (SEQ ID NO: 2) of exon 2 of an eIF4E gene on chromosome 3 of tomato, preferably in the nucleotide sequence AGGGTAAATCTGATACCAGC (SEQ ID NO: 3) in exon 2, and may include a mutation other than the mentioned mutations (e.g., substitution of one or more nucleotides in a nucleotide sequence(s) of SEQ ID NO: 2 and/or SEQ ID NO: 3). In one aspect, the mutated eIF4E gene has a mutation selected from the group consisting of: insertion of one nucleotide between the nucleotides at positions 15 and 16 (in one aspect, insertion of C (cytosine)); deletion of the three nucleotides at positions 16 to 18; and deletion of any nine nucleotides of the nucleotides at positions 8 to 18 (preferably, deletion of the nine nucleotides other than the nucleotides at positions 10 and 13), in the nucleotide sequence AGGGTAAATCTGATACCAGC (SEQ ID NO: 3) in exon 2 of an eIF4E gene on chromosome 3 of tomato, and may include a mutation other than the mentioned mutations. The nucleotide sequence of SEQ ID NO: 3 corresponds to the nucleotides at positions 135 to 154 of the nucleotide sequence (SEQ ID NO: 2) of exon 2 of tomato.

In one aspect, the mutated eIF4E gene is preferably such that the nucleotide sequence AGGGTAAATCTGA- TACCAGC (SEQ ID NO: 3) in exon 2 of an eIF4E gene on chromosome 3 of tomato has been mutated into any of SEQ ID NOs: 4 to 9.

As described above, the CMV-resistant gene of the present embodiments may include a mutation other than the above ones as long as desired CMV resistance is exhibited, and in one aspect, for example, may include any of the above mutations in a nucleotide sequence having a sequence identity of 85% or higher, preferably of 90% or higher, more preferably of 95% or higher, even more preferably of 98% or higher, particularly preferably of 99% or higher, to the nucleotide sequence of an eIF4E gene.

The present embodiments also relate to use of the mutated eIF4E gene for imparting CMV resistance to a solanaceous plant, and the mutated eIF4E gene itself as a CMV-resistant gene.

A CMV-resistant plant having the CMV-resistant gene can be obtained in various manners, without limitation, which are roughly classified into two methods exemplified as follows.

(1) Direct genome editing: a mutation is introduced just to an intended position through direct genome editing of a plant having eIF4E functional to CMV to produce a plant having a CMV-resistant gene.

(2) Gene mutagenesis: this is a method combining the following (A) and (B). (A): A CMV-resistant gene is produced, which is introduced into a plant with an appropriate promoter. (B) Of endogenous eIF4E possessed by a plant, eIF4E functional to CMV is made nonfunctional for CMV.

Now, the methods will be described.

The method (1) can be performed by using a known genome editing technique with site-specific nuclease such as CRISPR and TALEN. If a double-strand breakage is introduced with a restriction enzyme capable of cleaving a specific site of a genome, repair error occurs in repair of the double-strand breakage to introduce various mutations, which results in mutation of a gene encoding eIF4E functional to CMV into a CMV-resistant gene.

To introduce a mutation with particularly high specificity and high efficiency, a CRISPR system can be preferably used, and a CRISPR/Cas9 system can be particularly preferably used. In this system, a guide RNA (sgRNA) including a sequence that is complementary to a target gene and consists of about 20 nucleotides recognizes the target, Cas9 protein cleaves the duplex, and repair error occurs in repair of the breakage through the non-homologous end-joining (NHEJ) repair pathway, introducing a mutation to the target site.

Delivery of Cas protein and sgRNA into a plant can be performed via vectors encoding them by using a method known to those skilled in the art, such as an *Agrobacterium* method, a standard transfection method, an electroporation method, and a particle bombardment method.

To deliver Cas protein and sgRNA into a plant in a simple manner, as shown in Examples described later, binary vectors incorporating a Cas gene and sgRNA are constructed, with which *Agrobacterium* is transformed, and a plant is then transformed by using this *Agrobacterium* (e.g., see Friedrich Fauser et al. The Plant Journal (2014) 79, 348-359, Ohsawa, Ryo and Ezura, Hiroshi (2013), NBT (new plant breeding techniques), International Academic Publishing Co., Ltd.).

The form of a plant to be transformed with *Agrobacterium* is not limited to a particular form and may be any form that allows repair of the plant body, and examples thereof include cells under suspension culture, protoplasts, sections of a leaf, and calli. After *Agrobacterium* cells are removed, culture is performed with a chemical agent corresponding to the vector used, and sections incorporating the target gene can be subjected to selective culture with considering drug resistance as an indicator.

A guide RNA can be designed so that a mutation can be introduced to a target site with high efficiency.

The CRISPR system basically cleaves at the third nucleotide before a sequence of three nucleotides (NGG in using *S. pyogenes*-derived Cas9, which is the most common), which is called a PAM sequence. A PAM sequence needs to be present immediately after a target sequence, and hence a guide RNA can be designed so that a target sequence is positioned in the upstream of a PAM sequence. For example, with reference to FIG. 1, which shows a sequence corresponding to mRNA of an eIF4E gene present on chromosome 3 of tomato (SEQ ID NO: 1), a guide RNA can be designed so that the portion indicated by a rectangle present in exon 2 (the wavy portion in FIG. 1, SEQ ID NO: 2) is a PAM sequence, and 20 nucleotides, in typical cases, in the upstream from the three nucleotides (SEQ ID NO: 3) are target. When direct genome editing for another plant belonging to the family Solanaceae is performed to produce a plant having a CMV-resistant gene, a PAM sequence is selected, as with the case of tomato, from exon 2 of a gene encoding eIF4E functional to CMV to design a guide RNA, and a mutation is introduced to the target site.

A guide RNA can be designed with considering GC content because the higher the GC content of the nucleotide sequence of a guide RNA is, the higher the cleavage efficiency is. In addition, the guide RNA can be designed so as to reduce non-specific cleavages due to off-target effect as much as possible. In one aspect, in the case that the plant is tomato, a guide RNA can be designed so as to include a nucleotide sequence targeting a specific sequence in exon 2 on chromosome 3 (SEQ ID NO: 3).

When one double-strand breakage is introduced by the CRISPR system, about 20 nucleotides are repaired and repair error is inferred to occur to introduce a mutation. Accordingly, in one aspect, the mutation possessed by the CMV-resistant gene of the present embodiments is mutations of continuous or noncontinuous 3n nucleotides (n=1 to 7, preferably 1 to 3).

Next, the method (2) will be described. This method is a method combining the steps (A) and (B) below. Regarding the order of (A) and (B) to be performed, (B) may be performed first unless the plant dies. The method (1) is a method to perform only (B) for a specific site.

(A) A step of producing a mutated gene encoding an eIF4E protein nonfunctional for CMV, and introducing it into a plant with an appropriate promotor.

Production of a mutated gene in (A) can be performed by using a technique known to those skilled in the art. For example, a mutated gene can be obtained by synthesizing a nucleotide sequence having a desired mutation and amplifying it through PCR or the like. In addition, introduction of a mutated gene produced into a plant can be performed by using a technique known to those skilled in the art. Introduction of a mutated gene can be performed simply, for example, by using a polyethylene glycol method, an electroporation method, an *Agrobacterium* method, or a particle gun method, with a vector containing a mutated gene. As long as the CMV-resistant gene is obtained by mutating an eIF4E gene derived from a solanaceous plant, a CMV-resistant gene derived from another plant species may be introduced.

(B) A step of making eIF4E functional to CMV, among endogenous eIF4E possessed by a plant, into eIF4E nonfunctional for CMV.

In performing (B), a known method of introducing a mutation into a plant can be used, and, for example, mutagen treatment such as an ion beam and EMS can be used. In addition, (B) can be performed by using a genome editing technique such as the above-described CRISPR and TALEN. It is desirable to make all eIF4E functional to CMV, among endogenous eIF4E, into eIF4E nonfunctional for CMV.

Regeneration of a plant body from plant cells having a CMV-resistant gene can be performed with a method known to those skilled in the art according to the type of the plant. For example, regeneration of a plant body can be performed with reference to Sun H J et al., Plant Cell Physiol. 47: 426, 2006 for tomato, and to Jefferson R A et al., EMBO J. 6: 3901, 1987 for tobacco.

To confirm that a plant has a CMV-resistant gene, CMV is inoculated by using a conventional method as described above and the accumulation of CMV in the plant body is examined, for example, through an ELISA method or PCR, or the plant body is observed for symptoms of CMV infection.

Once a CMV-resistant plant having a CMV-resistant gene is obtained, a progeny or clone of the plant can be obtained by using a known technique. Thus, the scope of the CMV-resistant plant of the present embodiments includes progenies and clones thereof.

The present embodiments further relate to a method for producing a CMV-resistant plant, the method comprising mutating an eIF4E gene of a solanaceous plant. The method can be performed with reference to the above description regarding the CMV-resistant plant. In one aspect, the production method further includes a step of self-pollination or cross-pollination of the CMV-resistant plant of the present embodiments to obtain a progeny. Self-pollination or cross-pollination of a plant can be performed by using a known technique.

The present embodiments also relate to a guide RNA and a vector including a guide RNA for producing the above CMV-resistant plant. The guide RNA has the sequence as described above. The present embodiments further relate to a kit including the guide RNA. The kit can include site-specific nuclease or the like required to perform genome editing with the CRISPR system, and can be used for producing a CMV-resistant plant.

EXAMPLES

[Example 1] Production of Tomato Including Mutation Introduced to eIF4 Gene on Chromosome 3

Figures 1, 9:
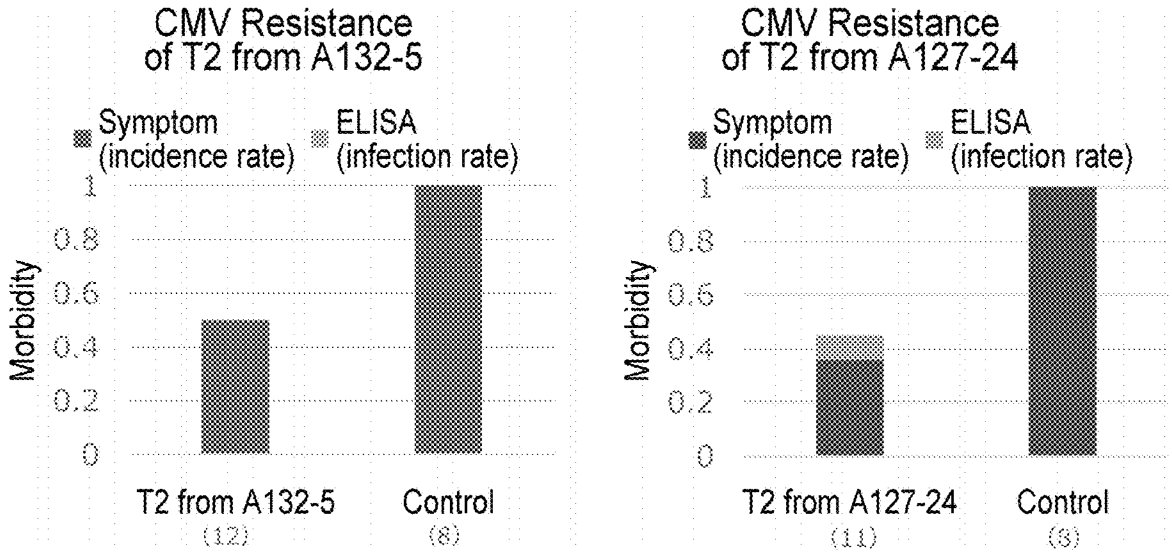
Figures 2, 9, 10:
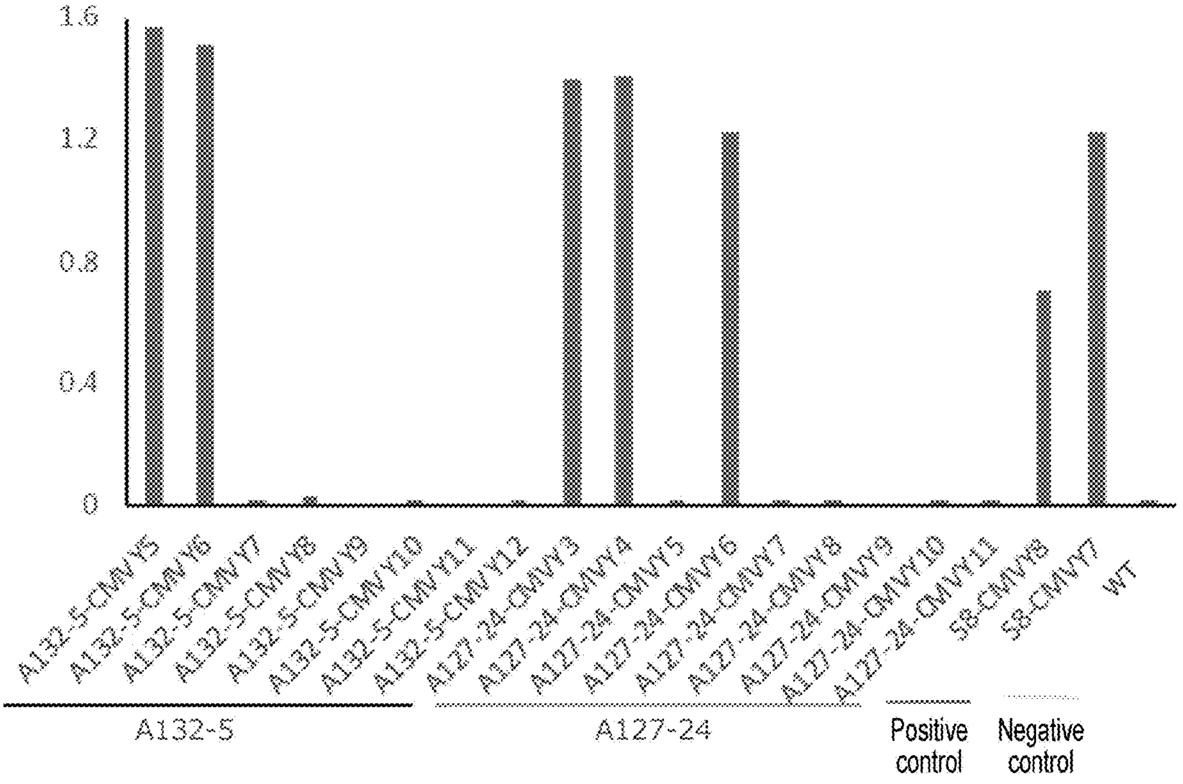

First, a site recognizable for sgRNA was arbitrarily set in the second exon (SEQ ID NO: 2) of an eIF4E gene (Solyc03g005870) believed to be present on chromosome 3 of tomato, and this double-stranded DNA of 20 nucleotides in length (AGGGTAAATCTGATACCAGC (SEQ ID NO: 3)) was constructed at a site for the restriction enzyme BbsI in the vector pUC19_AtU6oligo (obtained from National Institute of Agrobiological Sciences). FIG. 1 shows a nucleotide sequence corresponding to the mRNA sequence of eIF4E present on chromosome 3 of a wild-type plant of tomato (SEQ ID NO: 1). In the actual RNA, T (thymine) in the figure is U (uracil).

A cassette site including the sgRNA sequence region was cut out of the vector, and constructed at a site for the restriction enzyme I-SceI in the binary vector pZD_OsU3gYSA_HolgerCas9_NPTII. Further, the *Agrobacterium* LBA4404 (produced by Takara Bio Inc.) was transformed with the binary vector.

For an eIF(iso)4E gene (Solyc09g090580) present on chromosome 9 of tomato, a recognition site (GGCCACCGAAGCACCGGTAG (SEQ ID NO: 10)) in the second exon was constructed in a binary vector in the same manner, and *Agrobacterium* was transformed therewith.

For the varieties of tomato to be transformed, Moneymaker and the private inbred variety S were used. Transformation of tomato with *Agrobacterium* was in accordance with a method cited in common books or the like (Protocols for Plant Transformation (Kagaku-Dojin Publishing Company, INC.)). Specifically, pieces of cotyledons obtained from seeds of tomato seeded in a sterile medium, or pieces of cotyledons or pieces of true leaves obtained by normal seeding followed by sterilization were soaked in the above-described recombinant *Agrobacterium* culture solution (turbidity: 0.1 to 1.0) for about 10 minutes to infect with *Agrobacterium.*

Three days thereafter, *Agrobacterium* cells were removed, and the pieces of leaves were transferred in a Murashige and Skoog medium (MS medium: MS base, 3% sucrose, 1.5 mg/L zeatin, 1% agar) with carbenicillin (100 to 500 mg/mL), or with Meropen (20 to 50 mg/mL) and kanamycin (30 to 100 mg/mL), and subjected to selective culture at 25° C. under fluorescent light (light for 16 hours/dark for 8 hours). Thereafter, the medium was replaced through passage by transplantation every about 10 days to 2 weeks to promote callus formation from the pieces of leaves, and passage culture was subsequently repeated to induce adventitious shoots.

When an adventitious shoot grew to reach around several centimeters, the adventitious shoot was transplanted in a rooting medium (MS base, 1.5% sucrose, 1% agar, 50 to 250 mg/mL carbenicillin, 20 to 100 mg/mL kanamycin, optionally with naphthaleneacetic acid (NAA)), and cultured for 1 to 3 months with passage every month.

The processes before and including the culture in the rooting medium culture were all sterile culture. A plant with rooting was taken from the sterile medium, and transplanted and grown in nursery pot soil containing a mixture of commercially available black earth, red ball earth, and so on.

To determine whether the regenerated plants (transgenic first generation: hereinafter, referred to as T0) were recombined and edited (deletion, insertion, or substitution of a nucleotide), PCR (KODPlus Neo/TOYOBO CO., LTD.) was performed for amplification by using arbitrary primers, for example, primer 1 (ATCCATCACCCAAGCAAGTTAATT (SEQ ID NO: 11)) and primer 2 (GTCCACAAAGCTATTTTTTCTCCC (SEQ ID NO: 12)) for a region in Solyc03g005870, and primer 3 (CCGTCGTGAAAAAGCTATACAAAAGGAG (SEQ ID NO: 13)) and primer 4 (GCTTTTCGAAGAGAACTTCCCC (SEQ ID NO: 14)) for a region in Solyc09g090580, and examination was made on whether a restriction site present in an edited site of each amplified fragment was cleaved by a restriction enzyme (data not shown).

The results confirmed that the sequence of eIF4E had been edited in some of the regenerated plants, and edited strains were selected out (Table 1).

TABLE 1

| Name of edited strain | | | | | |
|---|---|---|---|---|---|
| | Name of strain (T0 generation) | | | | |
| | A127 | A132 | A143 | B95 | B100 |
| Variety | S | S | S | S | MM* |
| Target gene for editing | eIF4E | eIF4E | eIF4E | eIF(iso)4E | eIF(iso)4E |

*MM: Moneymaker

[Example 2] Confirmation Test for CMV Resistance of Mutated Tomato

Figure 3:
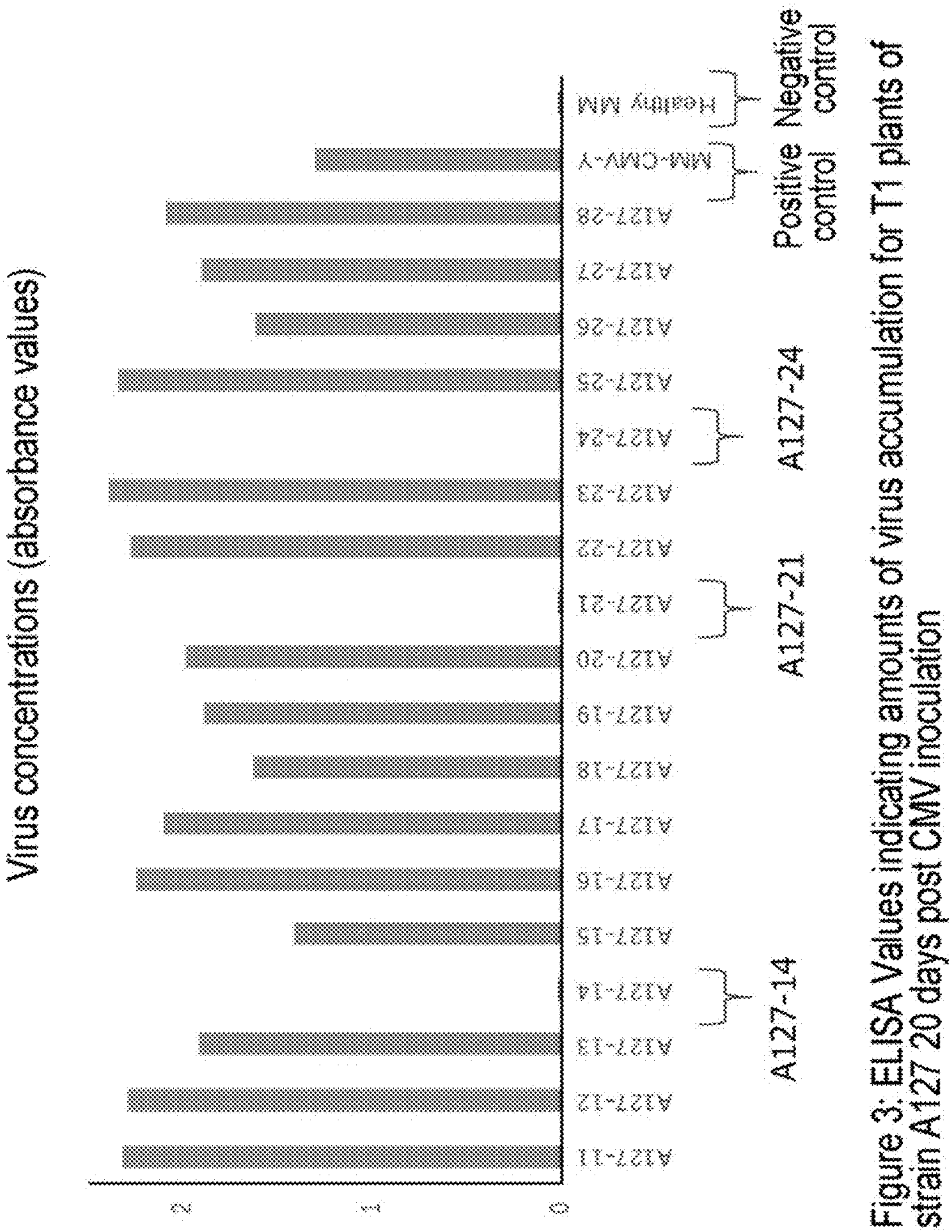
FIG. 3 shows a graph showing amounts of virus accumulation for 18 plants of the strain A127 (each being a T1 plant) 20 days after CMV inoculation. ELISA values (absorbance values) were measured with an anti-CMV antibody, and A127-14, A127-21, and A127-24 were found to have CMV resistance.
Figure 4:
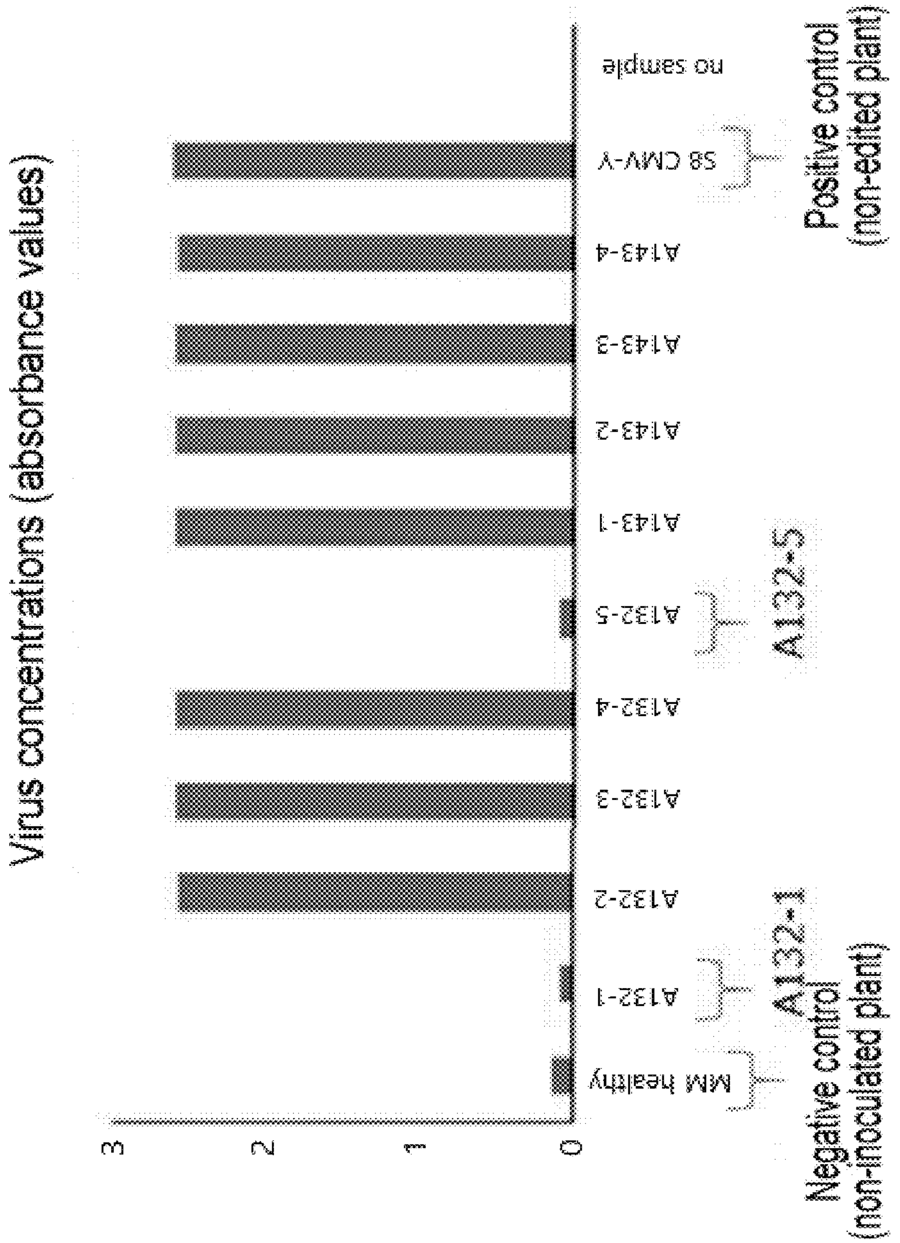
FIG. 4 shows a graph showing amounts of virus accumulation for five plants of the strain A132 and four plants of the strain A143 (each being a T1 plant) 30 days after CMV inoculation. ELISA values (absorbance values) were measured with an anti-CMV antibody, and A132-1 and A132-5 were found to have CMV resistance.
Figure 5:
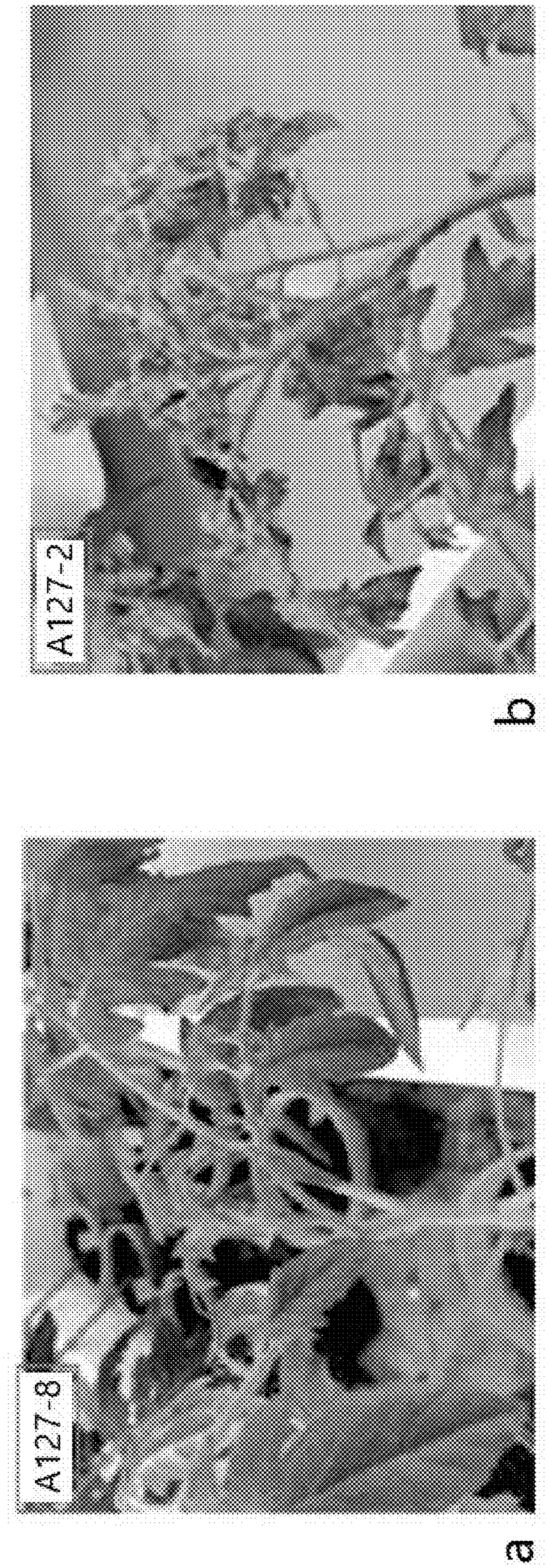
FIG. 5 shows photographs showing symptoms of T1 plants of the strain A127 23 days after CMV inoculation.

Next, plants (T0) of each edited strain were grown in an isolated greenhouse, and self-pollinated to collect seeds. These seeds as a transgenic progeny (T1) were seeded and then, seedlings were mechanically inoculated with the strain CMV-Y. As a result, no symptom was found for T1 plants of the eIF4E-edited strains A127 and A132, specifically, A127-8, A127-14, A127-21, A127-24, A132-1, and A132-5, even 20 days or more after the inoculation (FIG. 5). After 20 days or more from the CMV inoculation, ELISA to measure the degree of virus accumulation was performed with an anti-CMV antibody (obtained from Japan Plant Protection Association). As a result, the degrees of virus accumulation were comparable to those of plants without inoculation, and thus infection by CMV was not found (FIGS. 2 to 4). The plants exhibited no disease sign even after the lapse of 60 days or more, indicating CMV resistance (Table 2).

TABLE 2

| Examination of disease symptoms by CMV-Y inoculation test | | | | | | | | | |
|---|---|---|---|---|---|---|---|---|---|
| | Edited plant (T1) | | | | | | | | |
| | A127-8 | A127-14 | A127-21 | A127-24 | A132-1 | A132-5 | A127-7 | A143-3 | Control |
| Symptoms 21 days after inoculation | Non | Non | Non | Non | Non | Non | Mosaic Yellowing/fern leaves | Mosaic Yellowing/fern leaves | Mosaic Yellowing/fern leaves |
| Symptoms 60 days after inoculation | Non | Non | Non | Non | Non | Non | Mosaic Yellowing/fern leaves | Mosaic Yellowing/fern leaves | Mosaic Yellowing/fern leaves |
| Resistance | Presence | Presence | Presence | Presence | Presence | Presence | Non | Non | Non |

*Non-edited (nonrecombinant) variety S was used as the control

By contrast, T1 seedlings of the eIF(iso)4E-mutated strains B95 and B110 with CMV inoculation all presented with symptoms 20 days after the inoculation, indicating no resistance (data not shown).

[Example 3] Sequencing of CMV-Resistant Gene

With use of primers 1 and 2 described above, a portion around the eIF4E-edited site of a CMV-resistant T1 plant, specifically, a region in the 3'-side from around position 14 of the sequence of exon 2 (SEQ ID NO: 2) in the eIF4E gene on chromosome 3 was amplified through PCR (T100 Thermal Cycler, produced by Bio-Rad Laboratories, Inc.), and amplified fragments were cloned to examine the nucleotide sequence.

From the results, deletion, insertion, or substitution of several nucleotides was found in the same region (FIGS. 6-1, 6-2). Plants having a mutation as listed below in the region corresponding to SEQ ID NO: 3 were found. Each underline indicates a mutated portion, and "•" indicates a position without any nucleotide.

```
Wild-type:
                                   (SEQ ID NO: 3)
A G G G T A A A T C T G A T A • C C A G C

Mutation 1:
                                   (SEQ ID NO: 4)
A G G G T A A A T C T G A T A C C C A G C

Mutation 2:
                                   (SEQ ID NO: 5)
A G G G T A A A T C T G A T A • • • • G C

Mutation 3:
                                   (SEQ ID NO: 6)
A G G G T A A • • C • • A • • • • • • G C

Mutation 4:
                                   (SEQ ID NO: 7)
A G G G T A A A T G T G A T A • • • • G C

Mutation 5:
                                   (SEQ ID NO: 8)
A G T G T A A • • C • • A • • • • • • G C

Mutation 6:
                                   (SEQ ID NO: 9)
A G G G T A A A T G T A A C A • • • • G C
```

[Example 4] Confirmation Test for PVY Resistance

Figure 7:
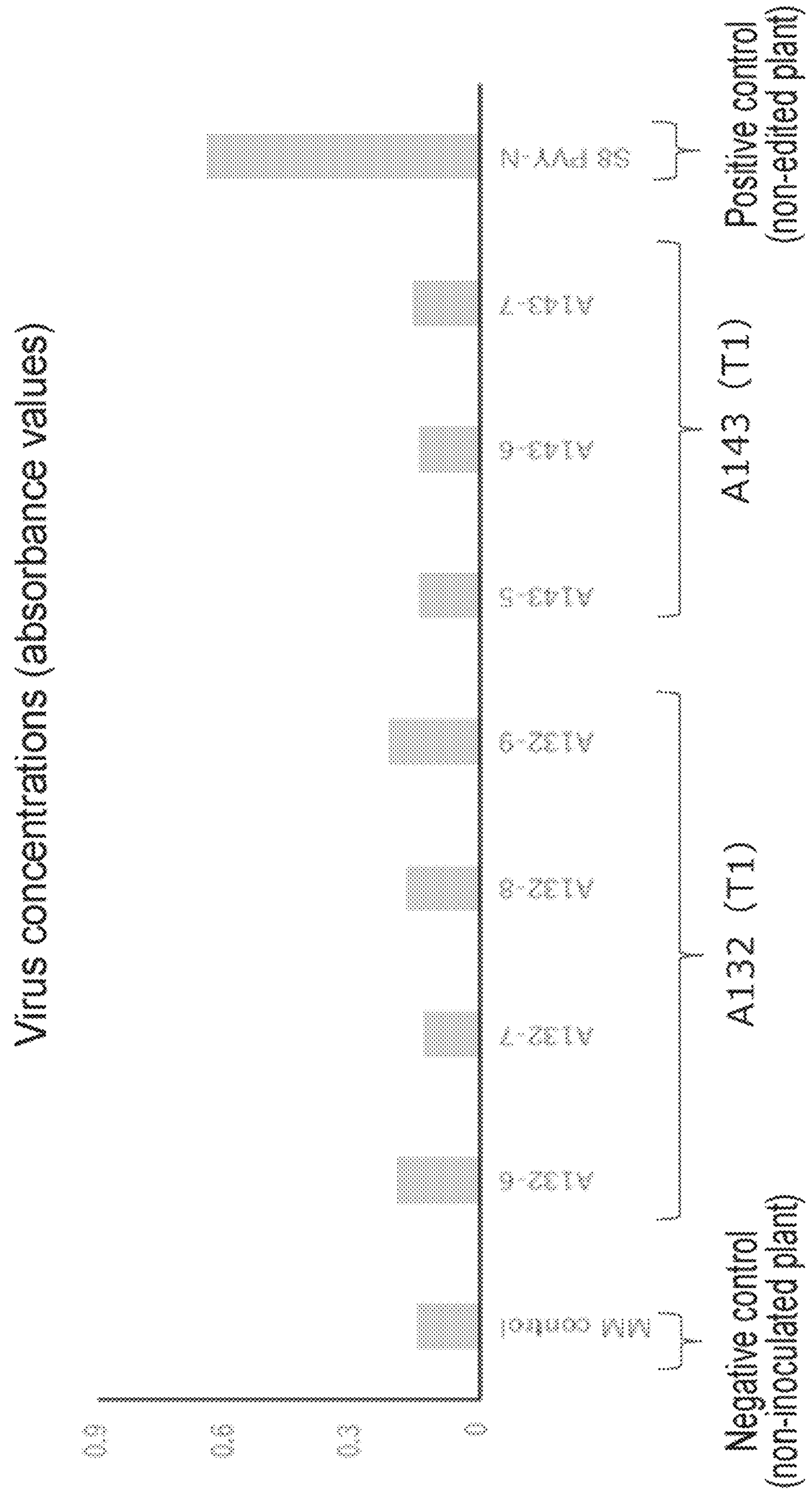
FIG. 7 shows a graph showing amounts of virus accumulation for four plants of the strain A132 and three plants of the strain A143 (each being a T1 plant) 24 days after PVY inoculation. ELISA values (absorbance values) with an anti-PVY antibody were measured, and all of the plants were found to have PVY resistance.

T1 seeds of A132 and A143 were separately seeded, and seedlings of them were inoculated with the strain PVY-N. Neither a symptom nor virus accumulation was found for all of the plants even after the lapse of 21 days or more after the inoculation, and thus PVY resistance was confirmed (FIG. 7).

[Example 5] Confirmation Test for CMV Resistance of Mutated Tomato (T2 Generation)—1

T1 plants obtained in Example 2, specifically, A127-24, A132-1, and A132-5, were grown in an isolated greenhouse in the same manner as in Example 2, and T2 seeds were collected after self-pollination.

Figure 8:
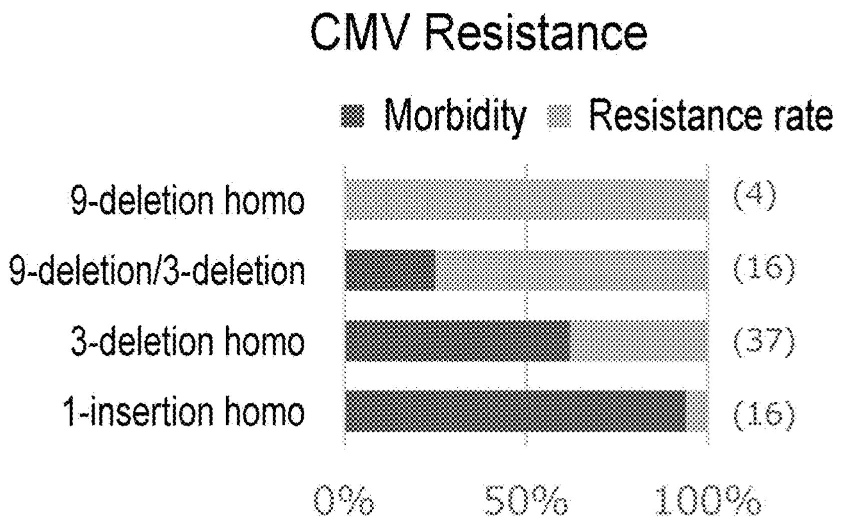
FIG. 8 shows a graph for determination of CMV resistance of each T2 generation in Example 5. Morbidities were determined on the basis of incidences determined by visual observation and infection rates determined by ELISA (degree of virus accumulation). Therefore, morbidities are comprehensive indicators including incidences and infection rates. Each number in parentheses indicates the number of plants tested.

These seeds as T2 generations were seeded, and seedlings of each T2 generation, the number of which was as shown in parentheses in the right column in FIG. 8, were mechanically inoculated with the strain CMV-Y. Examination of nucleotide sequences found that 16 plants of the T2 generation from A127-24 were all homo with insertion of one nucleotide (1-insertion homo). Thirty plants of the T2 generation from A132-1 included, as edit patterns, four plants of homo with deletion of nine nucleotides (9-deletion homo), 16 plants with deletion of nine nucleotides/deletion of three nucleotides (9-deletion/3-deletion), and 10 plants of homo with deletion of three nucleotides (3-deletion homo). Twenty-seven plants of the T2 generation from A132-5 were all 3-deletion homo. That is, in FIG. 8, "9-deletion homo" and "9-deletion/3-deletion" are derived from the T2 generation from A132-1, "3-deletion homo" from the T2 generations from A132-1 and A132-5, and "1-insertion homo" from the T2 generation from A127-24.

Twenty days after inoculation, CMV resistance was examined with the same technique as in Example 2. Specifically, virus morbidity was examined through observation of symptoms of infection and ELISA to measure the degree of virus accumulation. FIG. 8 shows the results. In FIG. 8, resistance rates are fractions of plants negative in the ELISA.

[Example 6] Confirmation Test for CMV Resistance of Mutated Tomato (T2 Generation)—2

Further, seedlings of T2 generations of A132-5, which was expected to be homo with deletion of three nucleotides, and A127-24, which was expected to be homo with insertion of one nucleotide, were mechanically inoculated with CMV-Y, and examined on resistance thereto in the same manner as in Example 5. In FIG. 9-1, each number in parentheses is the number of plants tested. Non-edited (nonrecombinant) wild-type plants (wild-type variety S) were used as a control. Twenty days after the inoculation, incidences were examined through observation of symptoms of infection and virus infection rates were examined through ELISA, and the results were combined into morbidity to determine CMV resistance. FIG. 9-2 shows results of measurement of virus infection through ELISA for some plants. Wild-type plants (wild-type variety S) with CMV inoculation were used as a positive control, and wild-type plants without CMV inoculation were used as a negative control. As shown in FIG. 9-1, all the T2 generations, from any of the plants including the T2 generation from A127-24 as 1-insertion homo, had higher virus resistance than the controls.

The results of Examples 5 and 6 confirmed that eIF4E mutation in any mutation pattern provided CMV resistance even for T2 generations.

[Example 7] Insect-Mediated Inoculation Test with Aphids

In actual fields, cucumber mosaic virus (CMV) is transmitted and infects primarily via aphids, as well as through seed transmission and contact transmission. For this reason, in addition to the mechanical inoculation tests, insect-mediated inoculation test with aphids was conducted to compare resistance with a control.

First, green peach aphids (*Myzus persicae*) were allowed to suck sap from tobacco infected with the strain CMV-O to acquire CMV.

Among the T2 generations from A132-1 obtained in Example 5, seeds of plants of homo with deletion of nine nucleotides (A132-1-13) were seeded to grow into seedlings with one or two true leaves, and 10 green peach aphids with CMV were released per seedling for insect-mediated inoculation.

Seedlings of the wild-type S were used as a control, and tested under the same conditions. Symptom test and RT-PCR were performed to calculate morbidity from day 21 to day 26 after the inoculation. Specifically, morbidity is an integrated value of incidence determined through visual observation and an infection rate determined through RT-PCR.

RT-PCR was performed by using primers 5 and 6 with enzymes (the reverse transcriptase AMV reverse transcriptase (produced by Promega Corporation) and EXTaq polymerase (produced by Takara Bio Inc.)). The results confirmed that the edited strain exhibited significantly lower morbidity than the control and thus had CMV resistance.

```
                                   (SEQ ID NO: 15)
Primer 5: GTACAGAGTTCAGGGTTGAGCG

                                   (SEQ ID NO: 16)
Primer 6: AGCAATACTGCCAACTCAGCTCC
```

INDUSTRIAL APPLICABILITY

The present invention enables to provide a CMV-resistant solanaceous plant and a method for producing a CMV-resistant plant. The present invention has industrial applicability primarily in the field of agriculture.

The invention claimed is:

1. A cucumber mosaic virus (CMV)-resistant solanaceous plant, which comprises a mutated eIF4E gene encoding an eIF4E protein nonfunctional for CMV, wherein the plant is a tomato plant, the mutated eIF4E gene is an eIF4E gene on chromosome 3 of the tomato plant, and the mutated eIF4E gene has one or more mutations selected from the group consisting of:

(a) an insertion of one nucleotide between the nucleotides at positions 15 and 16 of the eIF4E gene;

(b) a deletion of the three nucleotides at positions 16 to 18 in exon 2 of the eIF4E gene; and (c) a deletion of any nine nucleotides of the nucleotides at positions 8 to 18, in the nucleotide sequence AGGGTAAATCTGATACCAGC (SEQ ID NO: 3) in exon 2 of the eIF4E gene.

2. A method for producing a cucumber mosaic virus (CMV)-resistant plant, the method comprising mutating an eIF4E gene of a solanaceous plant to have one or more mutations to give a mutated eIF4E gene encoding an eIF4E protein that is nonfunctional for CMV, wherein the plant is a tomato plant, the mutated eIF4E gene is an eIF4E gene on chromosome 3 of the tomato plant, and the one or more mutations are selected from the group consisting of:

(a) an insertion of one nucleotide between the nucleotides at positions 15 and 16 of the eIF4E gene;

(b) a deletion of the three nucleotides at positions 16 to 18 in exon 2 of the eIF4E gene; and (c) a deletion of any nine nucleotides of the nucleotides at positions 8 to 18, in the nucleotide sequence AGGGTAAATCTGATACCAGC (SEQ ID NO: 3) in exon 2 of the eIF4E gene.

3. The cucumber mosaic virus (CMV)-resistant solanaceous plant according to claim 1, wherein the one or more mutations is (a) the insertion of one nucleotide between the nucleotides at positions 15 and 16 of the eIF4E gene.

4. The cucumber mosaic virus (CMV)-resistant solanaceous plant according to claim 1, wherein the one or more mutations is (b) the deletion of the three nucleotides at positions 16 to 18 in exon 2 of the eIF4E gene.

5. The cucumber mosaic virus (CMV)-resistant solanaceous plant according to claim 1, wherein the one or more mutations is (c) the deletion of any nine nucleotides of the nucleotides at positions 8 to 18, in the nucleotide sequence AGGGTAAATCTGATACCAGC (SEQ ID NO: 3) in exon 2 of the eIF4E gene.

6. The method according to claim 2, wherein the one or more mutations is (a) the insertion of one nucleotide between the nucleotides at positions 15 and 16 of the eIF4E gene.

7. The method according to claim 2, wherein the one or more mutations is (b) the deletion of the three nucleotides at positions 16 to 18 in exon 2 of the eIF4E gene.

8. The method according to claim 2, wherein the one or more mutations is (c) the deletion of any nine nucleotides of the nucleotides at positions 8 to 18, in the nucleotide sequence AGGGTAAATCTGATACCAGC (SEQ ID NO: 3) in exon 2 of the eIF4E gene.

* * * * *